| United States Patent [19] | [11] Patent Number: 4,789,744 |
|---|---|
| Russell | [45] Date of Patent: Dec. 6, 1988 |

[54] PROCESS FOR THE RESOLUTION OF ENANTIOMERIC ARYLOXYPHENOXY PROPIONATES

[75] Inventor: John W. Russell, Midland, Mich.

[73] Assignee: The Dow Chemical Company, Midland, Mich.

[21] Appl. No.: 81,518

[22] Filed: Aug. 5, 1987

[51] Int. Cl.$^4$ .................... C07D 211/72; C07B 57/00; C07C 67/60
[52] U.S. Cl. ...................................... 546/295; 560/62; 71/94; 71/109; 71/116; 562/401; 562/472
[58] Field of Search ................ 562/401, 472; 546/295; 560/62

[56] References Cited

U.S. PATENT DOCUMENTS 4,531,969  7/1985  Nestler et al. ........................ 71/108

OTHER PUBLICATIONS

Wainer, *Liquid Chromotography in Pharmaceutical Develop.; An Introduction*, pp. 68–80, (1985).
Wainer, *Chromatography Forum*, 1, (4), pp. 55–61, (1986).
Souter, CRC Press, Boca Raton, Fla., pp. 50, 75, 81, 146 and 189, (1985).
Jiang et al., *J. Chromatography*, 248, pp. 143–149, (1982).
Guyon et al., *J. Chromatography*, 152, pp. 551–556, (1978).

*Primary Examiner*—Werren B. Lone
*Assistant Examiner*—Vera C. Clarke
*Attorney, Agent, or Firm*—Craig E. Mixan; Ronald G. Brookens

[57] ABSTRACT

A process for the effective analytical or preparative resolution of the enantiomers of 2-(4-aryloxyphenoxy)-propionic acids or the $C_1$–$C_4$ alkyl esters thereof which comprises converting a racemic or partially resolved mixture of said 2-(4-aryloxyphenoxy)propionic acids or the $C_1$–$C_4$ alkyl esters thereof to a pair of diastereomeric terpene esters by reaction with an optically active terpene alcohol and separating the diastereomers of the terpene ester by liquid chromatography with a silica column.

3 Claims, No Drawings

PROCESS FOR THE RESOLUTION OF ENANTIOMERIC ARYLOXYPHENOXY PROPIONATES

BACKGROUND OF THE INVENTION

The herbicidal activity of aryloxyphenoxy propionic acids and derivatives thereof is well known in the art. Furthermore, optical isomers are often known to exhibit enhanced herbicidal activity over the corresponding racemates. For example, U.S. Pat. No. 4,531,969 has disclosed that the R-enantiomers of certain 2-(4-aryloxyphenoxy)propionic acids and certain derivatives thereof are distinguished by a considerably enhanced herbicidal action compared to the racemic modifications. Since reduced quantities of herbicide are required to achieve comparable levels of control, the application of mixtures enriched in the more efficacious R-enantiomer offers both economical and environmental advantages.

To exploit the agrinomic benefits of these advantages, it is necessary to efficiently resolve the racemic mixtures of the herbicides that are normally produced industrially and to accurately determine the ratio of the R- and S-enantiomers in the resulting composition.

Various methods for obtaining high concentrations of individual enantiomers are known. The most common method of resolution of a racemic modification involves its conversion by an optically active reagent into a mixture of diastereomers which can then be separated on the basis of their different physical properties. Diastereomers are generally separated by fractional crystallization, though occasionally by fractional distillation or chromatography. Once the diastereomers have been separated, they can be reconverted to the individual enantiomers and the optically active resolving agent can be recovered.

Unfortunately, the differences in physical properties of the diastereomers are rarely if ever great enough to effect a total separation with one crystallization. Usually repeated crystallizations must be used and the process is long and tedious. The same situation generally applies to differential boiling points and differential absorption with respect to distillation and chromatographic separations.

SUMMARY OF THE INVENTION

The present invention provides a process for the effective analytical or preparative resolution of the enantiomers of 2-(4-aryloxyphenoxy)propionic acids of formula (I)

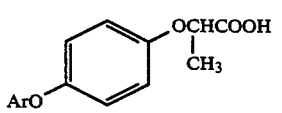

wherein
Ar is

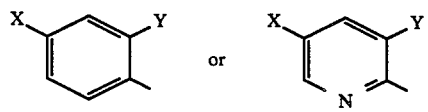

and X is $CF_3$, F, Cl, Br or I
and Y is H, F, Cl, Br or I
or the $C_1$-$C_4$ alkyl esters thereof which comprises converting a racemic or partially resolved mixture of said 2-(4-aryloxyphenoxy)propionic acid or $C_1$-$C_4$ alkyl ester thereof to a pair of diastereomeric terpene esters by reaction with an optically active terpene alcohol and separating the diastereomers of the terpene ester by liquid chromatography with a silica column. After separation the individual enantiomers of (I) can be recovered by hydrolysis of the separated terpene ester diastereomers.

This procedure allows the efficient separation of the enantiomers of 2-(4-aryloxyphenoxy)propionic acids to produce high optical purity materials of greater herbicidal activity than the unresolved racemates. Additionally, the method is useful for the accurate determination of the enantiomeric content of commercial compositions.

Any naturally occurring, optically active terpene alcohol is contemplated as the resolving agent. Relatively inexpensive d-menthol and l-menthol are the preferred embodiments.

The diastereomeric terpene esters to be separated can be prepared by a variety of methods, either with or without a solvent. However, it is important that the chosen methods do not cause racemization of the chiral center. For example, the racemic or partially resolved 2-(4-aryloxyphenoxy)propionic acid (I) can be treated with excess thionyl chloride to form the acid chloride. Removal of excess thionyl chloride followed by reaction of the acid chloride at elevated temperatures with a terpene alcohol, for example, d-menthol or l-menthol, provides a product consisting of a pair of diastereomeric esters. Alternatively, the 2-(4-aryloxyphenoxy)propionic acid (I) can be directly esterified with the terpene alcohol by standard procedures, preferably in the presence of a dehydrating agent such as 2,2-dimethoxypropane.

Similarly, the $C_1$-$C_4$ alkyl esters of 2-(4-aryloxyphenoxy)propionic acids (I) can be transesterified with the terpene alcohol by conventional techniques. Alternatively, the esters can be initially hydrolyzed to the acid which can be further converted to the diastereomeric terpene esters as described hereinabove.

The pair of diastereomeric terpene esters can be separated on a silica liquid chromatographic column. Silica is advantageously employed because it is relatively inexpensive and stable. The silica particle size may vary from 1 to 500μ. Particle sizes of from 5 to 150μ are preferred. Best resolutions are obtained by using particles of a narrow range, for example, less than ±10μ.

The column size is limited only by mechanical considerations. Those skilled in the art will appreciate the limitations on column size imposed by the scale of the operation. In general, the diastereomer weight load into the chromatographic system is limited by the capacity of the silica packing. More loading results in less resolution.

The eluents employed are simple and non-optically active. As is well known to those skilled in the art, the choice of eluents greatly affects the separation. Various components and concentrations of these components can be used. The optimal choice of eluent is dictated by the compounds to be separated and the column characteristics. Mixtures of hydrocarbons and halogenated hydrocarbons are preferred to achieve the desired separation.

Various eluent flow rates can be used limited by the pressure limitations of the chromatographic system. Optimum flow rates can be readily determined by procedures well known to those skilled in the art.

After the diastereomeric terpene esters have been separated, hydrolysis of the individual esters provides both the R- and S-enantiomers of exceedingly high optical purity. The more herbicidally active R-2-(4-aryloxyphenoxy)propionic acid may be esterified using conventional ester formation procedures to produce agriculturally acceptable esters which include the following: methyl, ethyl, propyl, butyl, octyl, ethoxyethyl, butoxyethyl and methoxypropyl.

The less herbicidally active S-enantiomer is preferably racemized by heating in the presence of a strong base and recycling the resulting racemate to the separation process.

DETAILED DESCRIPTION OF THE INVENTION

The following examples illustrate the invention.

EXAMPLE 1

Separation of R-2-(4-((3-fluoro-5-trifluoromethyl-2-pyridinyl)oxy)-phenoxy)propionic acid A racemic mixture of 2-(4-((3-fluoro-5-trifluoromethyl-2-pyridinyl)oxy)phenoxy)propionic acid was treated with an excess of thionyl chloride at 55° C. to form the acid chloride. Excess thionyl chloride was removed and a 5 mole percent excess of l-menthol was added and the mixture was heated at 55° C. for 2 hours with stirring. The product, which consisted of a pair of diastereomeric l-menthol esters, was dissolved in methylene chloride and injected into a preparative liquid chromatographic system.

INJECTION: 100 mg (milligrams) 2-(4-((3-fluoro-5-trifluoromethyl-2-pyridinyl)oxy)phenoxy)propionic acid, l-menthol ester diastereomers.

COLUMN: 1 m (meter)×4.6 mm (millimeter) ID packed with 30μ particle size, 60 Å pore size, 500–550 m²/g surface area silica (supplied by Sigma Chemical).

ELUENT: 20 percent (½ water saturated) ethylene dichloride; 80 percent hexane (v/v).

FLOW RATE: 2.0 mL/min

DETECTION: UV 280 nm

The cuts were collected at varying intervals of one to several minutes. Since flow rate was 2.0 mL/min, time of collection is easily ascertained from the cumulative volume data in Table I. The collected cuts were analyzed for enantiomer composition.

TABLE I

| Cumulative Volume, mL | R/S Ratio | % R, of Total R | % S, of Total S |
|---|---|---|---|
| 0–74 | — | 0 | 0 |
| 74–88 | 100/0 | 53.0 | 0 |
| 88–92 | 95.8/4.2 | 12.6 | 0.5 |
| 92–97 | 47.4/52.6 | 8.0 | 8.8 |
| 97–102 | 36.1/63.9 | 5.7 | 10.0 |
| 102–108 | 33.7/66.3 | 5.1 | 10.0 |
| 108–116 | 31.2/68.8 | 5.7 | 12.4 |
| 116–126 | 26.9/73.1 | 4.8 | 13.0 |
| 126–136 | 21.2/78.8 | 3.0 | 11.0 |
| 136–146 | 13.2/86.8 | 1.4 | 9.0 |
| 146–158 | 4.0/96.0 | 0.4 | 9.4 |
| 158–170 | 1.0/99.0 | 0.08 | 7.4 |
| 170–194 | 0.9/99.1 | 0.07 | 7.3 |

TABLE I-continued

| Cumulative Volume, mL | R/S Ratio | % R, of Total R | % S, of Total S |
|---|---|---|---|
| 194–220 | 3.9/96.1 | 0.04 | 1.0 |

The R-form of the l-menthol ester of the propionic acid was isolated in a 65.6 percent yield. After hydrolysis, R-2-(4-((3-fluoro-5-trifluoromethyl-2-pyridinyl)oxy)phenoxy)propionic acid of at least 99.7 percent R configuration was obtained.

Similar results were achieved using d-menthol, in which case the order of elution of the R- and S-forms was reversed.

EXAMPLE 2

Example 1 was repeated except that 50 mg of sample instead of 100 mg were injected. The results are summarized in Table II.

TABLE II

| Cumulative Volume, mL | R/S Ratio | % R, of Total R | % S, of Total S |
|---|---|---|---|
| 0–92 | — | 0 | 0 |
| 92–114 | 100/0 | 72.2 | 0 |
| 114–118 | 98.6/1.4 | 11.1 | 0.16 |
| 118–122 | 48.6/51.4 | 6.0 | 6.2 |
| 122–128 | 24.1/75.9 | 4.5 | 14.0 |
| 128–134 | 19.4/80.6 | 3.1 | 12.5 |
| 134–140 | 13.6/86.4 | 1.8 | 11.4 |
| 140–148 | 6.9/93.1 | 1.0 | 13.6 |
| 148–158 | 2.0/98.0 | 0.31 | 15.3 |
| 158–220 | 0/100 | 0 | 26.8 |

The R-form of the l-menthol ester of the propionic acid was isolated in an 83.3 percent yield. After hydrolysis, R-2-(4-((3-fluoro-5-trifluoromethyl-2-pyridinyl)oxy)phenoxy)propionic acid of at least 99.9 percent R configuration was obtained.

EXAMPLE 3

Example 1 was repeated except that a 30μ, 100 Å column was used and the eluent was changed to 20 percent ethylene dichloride/80 percent hexane absent ½ water saturation. The results are summarized in Table III.

TABLE III

| Cumulative Volume, mL | R/S Ratio | % R, of Total R | % S, of Total S |
|---|---|---|---|
| 0–48 | — | 0 | 0 |
| 48–62 | 100/0 | 49.4 | 0 |
| 62–67 | 62.0/38.0 | 13.8 | 8.6 |
| 67–73 | 40.1/59.9 | 9.3 | 14.3 |
| 73–79 | 37.7/62.3 | 7.3 | 12.3 |
| 79–83 | 35.3/64.7 | 5.7 | 10.6 |
| 83–91 | 32.7/67.3 | 4.5 | 9.4 |
| 91–97 | 38.8/61.2 | 5.3 | 8.6 |
| 97–103 | 25.1/74.9 | 2.2 | 6.7 |
| 103–109 | 19.7/80.3 | 1.4 | 5.9 |
| 109–115 | 10.3/89.7 | 0.6 | 5.6 |
| 115–121 | 6.2/93.8 | 0.3 | 4.4 |
| 121–127 | 2.9/97.1 | 0.1 | 3.8 |
| 127–137 | 2.0/98.0 | 0.1 | 5.2 |
| 137–160 | 1.2/98.8 | 0.05 | 4.6 |
| 160–184 | 0/100 | 0 | 0.1 |

EXAMPLE 4

The following separations (Table IV), expressed as α where $\alpha = (T_2 - T_0)/(T_1 - T_0)$ were obtained. $T_2$ is the retention time of the second diastereomer eluted. $T_1$ is the retention time of the first diastereomer eluted. $T_0$ is the retention time of unretained component. These separations were obtained using a 25 cm×4.6 mm ID, 5μ particle size silica column and a 2 mL/min flow rate of 20 percent ethylene dichloride/80 percent hexane (V/V eluent).

TABLE IV

Chromatographic Resolutions of

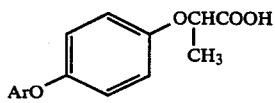

| Ar | Terpene Alcohol | α |
|---|---|---|
| CF$_3$—⟨pyridine⟩—F | l-menthol | 1.20 |
| CF$_3$—⟨pyridine⟩—F | d-menthol | 1.19 |
| CF$_3$—⟨pyridine⟩—F | (+)-isopinocampheol | 1.06 |
| CF$_3$—⟨pyridine⟩—F | (+)-isomenthol | 1.10 |
| CF$_3$—⟨pyridine⟩—Cl | l-menthol | 1.18 |

TABLE IV-continued

Chromatographic Resolutions of

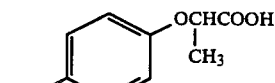

| Ar | Terpene Alcohol | α |
|---|---|---|
| Br—⟨phenyl⟩—F | l-menthol | 1.12 |

Various modifications may be made in the present invention without departing from the spirit or scope thereof, and it is understood that I limit myself only as defined in the appended claims.

What is claimed is:

1. A process for the resolution of the enantiomers of a 2-(4-aryloxyphenoxy)propionic acid of the formula

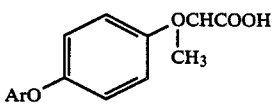

wherein
Ar is

X—⟨phenyl⟩—Y   or   X—⟨pyridyl⟩—Y and X is CF$_3$, F, Cl, Br or I
and Y is H, F, Cl, Br or I
or a C$_1$–C$_4$ alkyl ester thereof which comprises converting a racemic or partially resolved mixture of said 2-(4-aryloxyphenoxy)propionic acid or C$_1$–C$_4$ alkyl ester thereof to a pair of diastereomeric terpene esters by reaction with an optically active terpene alcohol and separating the diastereomers of the terpene esters by elution from a silica column with an eluent selected from the group consisting of hydrocarbons, halogenated hydrocarbons, water-saturated halogenated hydrocarbons and mixtures thereof.

2. The process of claim 1 wherein the optically active terpene alcohol is d-menthol or l-menthol.

3. The process of claim 1 wherein the individual enantiomers of the 2-(4-aryloxyphenoxy)propionic acid are recovered by hydrolysis of the separated terpene ester diastereomers.

* * * * *